United States Patent
Heidelberger

(10) Patent No.: US 7,934,498 B1
(45) Date of Patent: May 3, 2011

(54) DEVICE AND METHOD FOR FACILITATING DELIVERY OF MEDICATION/HUMIDITY TO A PATIENT WITHOUT BREAKING A VENTILATOR CIRCUIT

(76) Inventor: Robert Heidelberger, Kings Park, NY (US)

(*) Notice: Subject to any disclaimer, the term of this patent is extended or adjusted under 35 U.S.C. 154(b) by 1206 days.

(21) Appl. No.: 11/598,604

(22) Filed: Nov. 13, 2006

(51) Int. Cl.
*A61M 15/00* (2006.01)
*A61M 16/10* (2006.01)
*A61M 16/00* (2006.01)
*A61M 15/08* (2006.01)

(52) U.S. Cl. ......... 128/204.17; 128/203.12; 128/203.15; 128/203.19; 128/203.21; 128/203.22; 128/204.18; 128/200.24

(58) Field of Classification Search ............. 128/203.12, 128/203.15, 203.19, 203.21, 203.22, 204.18, 128/200.24

See application file for complete search history.

(56) References Cited

U.S. PATENT DOCUMENTS

| 3,990,442 A | 11/1976 | Patneau |
| 4,805,609 A | 2/1989 | Roberts et al. |
| 4,946,439 A | 8/1990 | Eggers |
| 5,277,175 A | 1/1994 | Riggs et al. |
| 5,355,872 A | 10/1994 | Riggs et al. |
| 5,388,571 A * | 2/1995 | Roberts et al. ........... 128/203.12 |

* cited by examiner

*Primary Examiner* — Patricia M Bianco
*Assistant Examiner* — Nihir Patel
(74) *Attorney, Agent, or Firm* — Richard L. Miller

(57) ABSTRACT

A device and method for facilitating the delivery of medication/humidity to a patient without breaking a ventilator circuit that contains a two-position flow control valve in the circuit, so as to permit manual switching from a first position in which humidified air/oxygen will be supplied to a patient and a second position in which atomized medication will be supplied to the patient.

2 Claims, 2 Drawing Sheets

Figure 1:
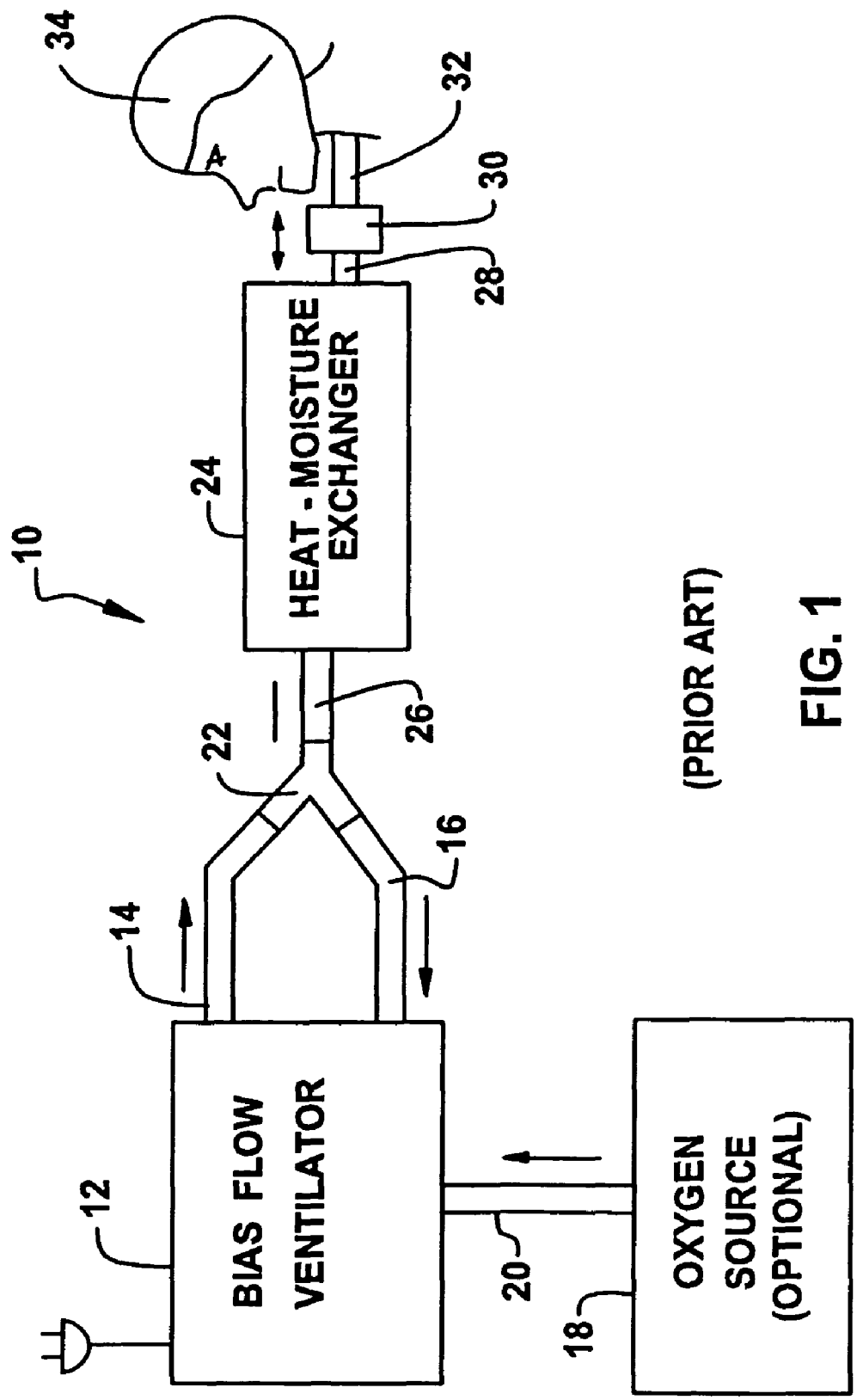

DEVICE AND METHOD FOR FACILITATING DELIVERY OF MEDICATION/HUMIDITY TO A PATIENT WITHOUT BREAKING A VENTILATOR CIRCUIT

BACKGROUND OF THE INVENTION

1. Field of the Invention

The present invention relates to a ventilation system, and more particularly, a device for facilitating the delivery of medication/humidity to a patient without breaking a ventilator circuit.

When patients can no longer breathe on their own, there is a medical option of using a ventilator to keep the patient breathing. In many cases, a patient stops breathing when many organs within the body fail due to disease. This is normally the time of death, but in some cases, a patient may choose to be kept alive on a ventilator. In certain diseases, the patient is fully aware and conscious, but the muscles used for breathing no longer function properly. Diseases of the nervous system such as A.L.S. (Lou Gehrig's Disease) can eventually cause total inability to move any part of the body, even the muscles of breathing. Some A.L.S. patients choose to be placed on a ventilator in order to stay alive.

Though more commonly known as life support devices, ventilators today do more than merely keep patients alive. They promote patient comfort, aid recovery from surgery and other medical conditions, prolong life for people with certain neuromuscular diseases (such as Lou Gehrig's disease), and, in cases such as Reeve's, allow patients to live at home and lead as nearly normal lives as possible. Ventilators are used by people of all ages, from premature infants to adults, who have any number of health problems that for one reason or another impair their ability to breathe normally.

Ventilators perform one of the most complex functions of the body ventilation, a process in which the lungs take in and disperse oxygen the body needs and gather up and expel the carbon dioxide created as a result of body functions. In healthy people, this gas exchange takes place in the small air sacs of the lungs, called alveoli, and in the course of one day, normally involves 8,000 to 9,000 liters of air breathed in through the nose or mouth and 8,000 to 10,000 liters of blood pumped through the lungs by the heart.

The idea of mechanical ventilation is now new. Earnest efforts date to the mid 1800's, when devices resembling steam cabinets and phone booths were used to maintain breathing by decreasing the air pressure inside the machine. A well known device that applied this negative pressure principle was the iron lung, when was widely used in the United States from the late 1920's into the 1950's, particularly for polio patients. However, these devices were large, and they greatly restricted patient movement.

In the late 1950's positive pressure ventilators, which force air into the lungs, were introduced. Like their predecessors, modern ventilators function to deliver breaths of oxygen enriched air to the body and remove carbon dioxide. But unlike in the past, most ventilators today are computer controlled, functioning in complex ways to produce positive pressure ventilation that more closely matches a patients breathing needs. Until about the early 1990's, modern ventilators required an artificial airway, usually a tube placed through a hole surgically created into the patient's throat or a tube passed through the patient's nose or mouth. More recently, noninvasive position pressure ventilators that allow for gas exchange through a face or nose mask have become popular.

Ventilators can be used for neuromuscular disorders, respiratory disorders and bone disorders. The neuromuscular disorders are amyotrophic lateral sclerosis (Lou Gehring's disease), Guillain-Barre syndrome, infant botulism, muscular dystrophies, myasthenia gravis, polio and post-polio related problems, spinal muscular atrophy and spinal cord injuries. The respiratory disorders are chronic obstructive pulmonary disease (concurrent emphysema, asthma and bronchitis), Pierre Robin syndrome (jaw disorder in newborns in which the tongue may fall backwards, obstructing breathing), cystic fibrosis, severe pneumonia and lung and chest injuries. The bone disorders are severe kyphoscoliosis (unusual curvatore of the spine), deformities of the chest wall and surgical removal or severe fracturing of ribs.

2. Description of the Prior Art

Numerous innovations for respiratory treatment devices have been provided in the prior art that will be described. Even though these innovations may be suitable for the specific individual purposes to which they address, however, they differ from the present invention.

A FIRST EXAMPLE, U.S. Pat. No. 3,990,442, Issued on Nov. 9, 1976, to Patneau teaches a device for the treatment of pulmonary ailments that includes an intermittent constant pressure breathing apparatus which simultaneously provides both humidified air and a nebulized medicant through a single breathing tube. The device is characterized as being very compact and portable and is adaptable to several modes of operation, including supplying humidified air alone, providing nebulized medicant alone, or simultaneously providing nebulized, humidified air and medicant. Various modes of operation may also include providing intermittent positive pressure breathing to a patient.

A SECOND EXAMPLE, U.S. Pat. No. 4,805,609, Issued on Feb. 21, 1989, to Roberts et al. teaches a novel ventilating system for human patients that includes a nebulizing means for nebulizing a liquid medication into a supply of humidified breathable gas under pressure. The nebulizing means comprises a nebulizing module having a cap portion to which is attached a vial-like nebulizing chamber. In order to maintain the hermetic integrity of the system a two-position, flow control valve assembly is operatively connected to and in selective flow communication with, a lower region of the vial-like, liquid-retention nebulizing chamber. The valve assembly is configured so that it can be manually actuated between a first position precluding access to the chamber or a second position for drainage of liquid from within the nebulizer chamber or addition of liquid to such chamber while maintaining system sealing and pressure. A liquid handling means such as a syringe is used to control withdrawal or addition of liquid.

A THIRD EXAMPLE, U.S. Pat. No. 4,946,439, Issued on Aug. 7, 1990, to Eggers teaches a dual source parenteral infusion system that includes a primary controller which controls the flow rate of a parenteral solution, a display which displays parameters associated with the delivery of a primary solution, and pushbuttons for entering solution delivery parameters into the controller. The primary controller communicates with a secondary infusion module which is programmed to deliver solution from a secondary source, with the flow rate being controlled by the primary controller. The secondary infusion module includes a display for displaying parameters associated with the delivery of the secondary solution and a drop detector, and mounts about a drip chamber for the secondary solution. The module may also include pushbuttons for entering fluid delivery parameters for the secondary solution into the module.

A FOURTH EXAMPLE, U.S. Pat. No. 5,277,175, Issued on Jan. 11, 1994, to Riggs et al. teaches a continuous flow nebulizing device for patients receiving long term nebulized medicant respiratory therapy. The nebulizing device comprises a nebulizer vial through which nebulizing fluids are delivered from a large supply vessel to conventional nebulizing apparatus. Thereby, the nebulizing apparatus connected to the continuously replenished nebulizer vial, delivers a larger volume of nebulized medicants on a continuous basis to a patient than can be provided by a conventional nebulizer vial without removing the conventional nebulizer vial from the nebulizer. For critically ill patients, the nebulizing device is used as part of a nebulizer/ventilator circuit. For voluntary respiratory patients, the nebulizer device output is used without a ventilator. Medicant supplying circuits are provided whereby a single medicant is selectably delivered from a plurality of large supply vessels without disconnecting the nebulizing vial from the nebulizer. Liquid level control circuits are provided whereby the level of liquid in the nebulizer vial is electrically or fluidically controlled. Nebulizing gas flow, synchronized with inhalation and exhalation rates, provides a plurality of options of aerosolized mist production patterns. Such synchronization is defined by a ventilator. An add-site device which provides direct access by a syringe needle into the nebulizer vial for addition of medicants and withdrawal of fluid is disclosed. Adjustable temperature control is provided for ventilating and nebulizeable fluids.

A FIFTH EXAMPLE, U.S. Pat. No. 5,355,872, Issued on Oct. 18, 1994, to Riggs et al. teaches a nebulizer device, comprising a housing defining an interior volume therewithin, including a reservoir portion for holding medicament therein for entrainment into a carrier gas to form a delivery gas mixture comprising nebulized medicament and carrier gas; a discharge port connected to the housing in flow communication with the interior volume therewithin, for discharging the delivery gas mixture from the housing; a jet passage member having an inlet portion for introduction of carrier gas thereinto and a nozzle portion positioned in the interior volume of the housing for discharging carrier gas in jet form in the interior volume, for entrainment of medicament from the reservoir portion of the housing in the carrier gas jet, such nozzle portion comprising a nozzle orifice accommodating carrier gas flow therethrough, wherein the nozzle orifice has an equivalent orifice diameter in the range of from about 0.005 inch to about 0.020 inch.

It is apparent now that numerous innovations for respiratory treatment devices have been provided in the prior art that are adequate for various purposes. Furthermore, even though these innovations may be suitable for the specific individual purposes to which they address, accordingly, they would not be suitable for the purposes of the present invention as heretofore described.

SUMMARY OF THE INVENTION

AN OBJECT of the present invention is to provide a device for facilitating the delivery of medication/humidity to a patient without breaking a ventilator circuit that avoids the disadvantages of the prior art.

ANOTHER OBJECT of the present invention is to provide a device for facilitating the delivery of medication/humidity to a patient without breaking a ventilator circuit that is simple and inexpensive to manufacture.

STILL ANOTHER OBJECT of the present invention is to provide a device for facilitating the delivery of medication/humidity to a patient without breaking a ventilator circuit that is simple to use.

BRIEFLY STATED, STILL YET ANOTHER OBJECT of the present invention is to provide a device for facilitating the delivery of medication/humidity to a patient without breaking a ventilator circuit that contains a two-position flow control valve in the circuit, so as to permit manual switching from a first port “B” in which humidified air/oxygen will be supplied to a patient and a second port “M” in which atomized medication will be supplied to the patient.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawings are briefly described as follows:

FIG. 1 is a diagrammatic block diagram showing the prior art; and

FIG. 2 is a diagrammatic block diagram showing an embodiment of the present invention.

A MARSHALLING OF REFERENCE NUMERALS UTILIZED IN DRAWING

Prior Art

3-10 typical ventilation circuit
12 bias flow ventilator of ventilation circuit 10
14 inspiratory ventilating conduit of bias flow ventilator 12
16 expiratory ventilating conduit of bias flow ventilator 12
18 optional oxygen source of ventilation circuit 10
20 feed conduit between bias flow ventilator 12 and optional oxygen source 18
22 ventilator Y-connector of ventilation circuit 10
24 heat-moisture exchanger of ventilation circuit 10
26 first flow conduit of heat-moisture exchanger 24
28 second flow conduit of heat-moisture exchanger 24
30 coupling member of ventilation circuit 10
32 breathing tube of ventilation circuit 10
34 patient

Present Invention

110 device
112 bias flow ventilator of device 110
114 inspiratory ventilating conduit of bias flow ventilator 112
116 expiratory ventilating conduit of bias flow ventilator 112
118 optional oxygen source of device 110
120 feed conduit between bias flow ventilator 112 and optional oxygen source 118
122 Y-connector of device 110
122*a* input port of the two position control valve
123 two-position flow control valve of device 110
124 heat-moisture exchanger of device 110
126 first flow conduit of heat-moisture exchanger 124
128 second flow conduit of heat-moisture exchanger 124
129 T-connector of device 110
130 coupling member of device 110
132 breathing tube of device 110
134 patient
136 nebulizer/metered dose inhaler of device 110
138 inlet conduit of nebulizer/metered dose inhaler 136
140 outlet conduit of nebulizer/metered dose inhaler 136

142 first check valve in inlet conduit 138
144 second check valve in outlet conduit 140
146 medication unit of device 110
148 port 148 for introducing additional medicine from medication unit 146

DETAILED DESCRIPTION OF THE PREFERRED EMBODIMENT

Referring now to the figures, in which like numerals indicate like parts, and particularly to FIG. 1, which is a diagrammatic block diagram showing the prior art, and as such, will be discussed with reference thereto.

The prior art is a typical ventilation circuit 10 which comprises a bias flow ventilator 12 having an inspiratory ventilating conduit 14 and an expiratory ventilating conduit 16 extending therefrom. An oxygen source 18 is optionally connected by a feed conduit 20 to the bias flow ventilator 12 to alternately supply an increased amount of oxygen and air instead of just air through the bias flow ventilatory 12. A ventilator Y-connector 22 is connected to the inspiratory ventilating conduit 14 and the expiratory ventilating conduit 16. A heat-moisture exchanger 24 has a first flow conduit 26 and a second flow conduit 28. The first flow conduit 26 is connected to the Y-connector 22. A coupling member 30 is connected to the second flow conduit 24. A breathing tube 32 is connected between the coupling member 30 and a patient, so that air/oxygen will travel through the heat-moisture exchanger 24 and into the lungs of the patient 34.

Figure 2:
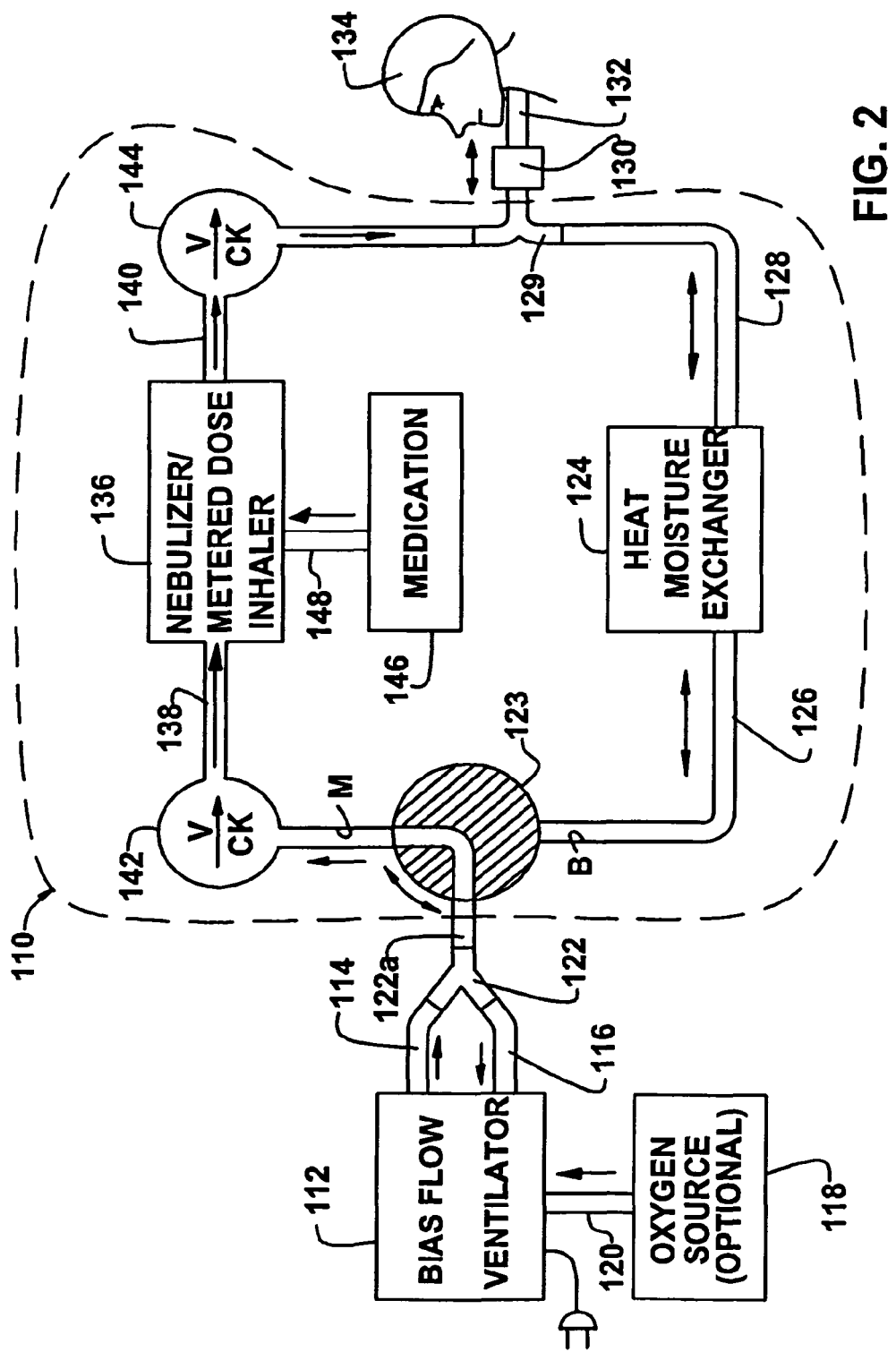

FIG. 2 is a diagrammatic block diagram showing an embodiment of the present invention, and as such, will be discussed with reference thereto. The present invention is a device 110 for facilitating the delivery of medication/humidity to a patient without breaking a ventilator circuit which from a bias flow ventilator 112 having an inspiratory ventilating conduit 114 and an expiratory ventilating conduit 116 extending therefrom. An oxygen source 118 is optionally connected by a feed conduit 120 to the bias flow ventilator 112 to alternately supply an additional amount of oxygen instead of just air through the bias flow ventilator 112. A Y-connector 122 is connected to the inspiratory ventilating conduit 114 and the expiratory ventilating conduit 116.

The device of the present invention is enclosed in the dotted curve indicated by arrow 110. A two position control valve 123 has an input port 122a connected to the Y-connector 122. A heat-moisture exchanger 124 has a first flow conduit 126 and a second flow conduit 128. The first flow conduit 126 is connected to the two-position flow control valve 123 shown located ninety degrees from the input port 122a of the two position control valve. A T-connector 129 is connected to the second flow conduit 128.

A coupling member 130 is connected to the T-connector 129. A breathing tube 132 is connected between the coupling member 130 and a patient 134. A nebulizer/metered dose inhaler 136 has an inlet conduit 138 and an outlet conduit 140. The inlet conduit 138 is in fluid communication with the two-position flow control valve 123 and shown ninety degrees from the input port 122a, of the two position control valve 123, opposite from the first flow conduit 126 of the heat-moisture exchanger 124. The outlet conduit 140 is in fluid communication with the T-connector 129. When the two-position flow control valve 123 is manually actuated to a first port "B" humidified air/oxygen will travel through the heat-moisture exchanger 124 and into the lungs of the patient 134. When the two-position flow control valve 123 is manually actuated to a second port "M" air/oxygen with atomized medication will travel through the nebulizer/metered dose inhaler 136 and into the lungs of the patient 134.

The device 110 further comprises a first check valve 142 within the inlet conduit 138 of the nebulizer/metered dose inhaler 136. A second check valve 144 is within the outlet conduit 140 of the nebulizer/metered dose inhaler 136. The first check valve 142 and the second check valve 144 will only let air/oxygen with atomized medication flow one way out through the nebulizer/metered dose inhaler 136 into the lungs of the patient 134. The nebulizer/metered dose inhaler 136 has a port 148 for introducing additional medicine into the lungs of the patient 134, from a medication unit 146.

Accordingly this arrangement of components allows a technician to medicate a patient 34 without opening the ventilating circuit 10, at the first flow conduit 26 and the second flow conduit 28, shown in FIG. 1 and substituting for the heat-moisture exchange 24 component a nebulizer/meter dose inhaler 136 component and then re-swap the components when the medication procedure is completed.

Instead it is only necessary to change the position of the two-position flow control valve 123 to switch the fluid flow path from a breathing path port B position to a medicating path port M position when a particular desired modality is required, that is normal breathing or breathing with medication.

In operative use the device 110 of the present invention allows for a method for facilitating the delivery of medication to a patient without breaking a ventilator circuit by employing the steps of:
1. connecting an input port 122a of a two position control valve 123 to a bias flow ventilator 112;
2. connecting an arm of a T-connector 129 to the breathing tube 132 of a patient 134;
3. activating the bias flow ventilator 112; and
4. switching a two position control valve from a position "B" causing a heat moisture exchanger 124 to be in fluid communication with said bias flow ventilator 112 to a position "M" causing a nebulizer/metered dose inhaler 136 to instead be in fluid communication with said bias flow ventilator 112.

In operative use the device 110 of the present invention also allows for a method for facilitating the delivery of non-medicated atmosphere to a patient without breaking a ventilator circuit by employing the following steps of:
1. connecting an input port of a two position control valve 122a to a bias flow ventilator 112;
2. connecting an arm of a T-connector 129 to the breathing tube 132 of a patient 134;
3. activating the bias flow ventilator 112; and
4. switching a two position control valve from a position "M" causing a nebulizer/metered dose inhaler 136 to be in fluid communication with said bias flow ventilator 112 to a position "B" causing a heat moisture exchanger 124 to instead be in fluid communication with said bias flow ventilator 112.

It should be noted that when examining FIG. 2, as shown, at a first glance the system appears to be inoperative because it would appear that there is no path for expired air to exit the system. However this is not the case because the heat moisture exchanger construction is such that normally expired air can exit this device when the first flow conduit 126 is restricted or blocked.

It will be understood that each of the elements described above, or two or more together, may also find a useful application in other types of constructions differing from the types described above.

While the invention has been illustrated and described as embodiments of a device for facilitating the delivery of medication/humidity to a patient without breaking a ventilator circuit, accordingly it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A device for facilitating the delivery of medication/humidity to a patient without breaking a ventilator circuit of a bias flow ventilator having a ventilator connector which comprises:
   A) a two-position flow control valve for connecting to said ventilator connector;
   B) a heat-moisture exchanger having a first flow conduit and a second flow conduit, wherein said first flow conduit is connected to a first port of said two-position flow control valve;
   C) a T-connector having a first arm connected to second flow conduit of said heat-moisture exchange, a second arm for fluidly communication with an outlet conduit of a nebulizer/metered dose inhaler and a third arm for connecting to a coupling member of a breathing tube of a patient; and
   D) said nebulizer/metered dose inhaler having an inlet conduit and a outlet conduit, said inlet conduit for fluidly communicating with a second port of said two-position flow control valve, and said outlet conduit is in fluid communication with said T-connector, so that when said two-position flow control valve is manually actuated to a first position humidified air/oxygen will travel through said heat-moisture exchanger and into the lungs of the patient, and when said two-position flow control valve is manually actuated to a second position air/oxygen with atomized medication will travel through said nebulizer/metered dose inhaler and into the lungs of the patient, further comprising:
   a) a first check valve within said inlet conduit of said nebulizer/metered dose inhaler; and
   b) a second check valve within said outlet conduit of said nebulizer/metered dose inhaler, wherein said first check valve and said second check valve will only let air/oxygen with atomized medication flow one way out through said nebulizer/metered dose inhaler into the lungs of the patient.

2. A device for facilitating the delivery of medication/humidity to a patient without breaking a ventilator circuit of a bias flow ventilator having a ventilator connector which comprises:
   A) a two-position flow control valve for connecting to paid ventilator connector;
   B) a heat-moisture exchanger having a first flow conduit and a second flow conduit, wherein said first flow conduit is connected to a first port of said two-position flow control valve;
   C) a T-connector having a first arm connected to said second flow conduit of said heat-moisture exchanger, a second arm for fluidly communication with an outlet conduit of a nebulizer/metered dose inhaler and third arm for connecting to a coupling member of a breathing tube of a patient; and
   D) said nebulizer/metered dose inhaler having an inlet conduit and a outlet conduit, said inlet conduit for fluidly communicating with a second port of said two-position flow control valve, and said outlet conduit is in fluid communication with said T-connector, so that when said two-position flow control valve is manually actuated to a first position humidified air/oxygen will travel through said heat-moisture exchanger and into the lungs of the patient, and when said two-position flow control valve is manually actuated to a second position air/oxygen with atomized medication will travel through said nebulizer/metered dose inhaler and into the lungs of the patient, further comprising said nebulizer/metered dose inhaler having a port for introducing additional medicine into said nebulizer/metered dose inhaler accordingly to the lungs of the patient.

* * * * *